(12) United States Patent
Braghiroli

(10) Patent No.: US 7,466,430 B2
(45) Date of Patent: *Dec. 16, 2008

(54) METHOD AND APPARATUS FOR OPTICALLY SCANNING A PNEUMATIC TIRE OF A VEHICLE WHEEL

(75) Inventor: Francesco Braghiroli, Reggio Emilia (IT)

(73) Assignee: Snap-On Equipment SRL a Unico Socio, Correggio (Reggio Emilia) (IT)

( * ) Notice: Subject to any disclaimer, the term of this patent is extended or adjusted under 35 U.S.C. 154(b) by 241 days.

This patent is subject to a terminal disclaimer.

(21) Appl. No.: 10/765,207

(22) Filed: Jan. 28, 2004

(65) Prior Publication Data

US 2005/0052657 A1  Mar. 10, 2005

(30) Foreign Application Priority Data

Sep. 4, 2003  (EP) .................................. 03020101

(51) Int. Cl.
*G01B 11/24* (2006.01)
(52) U.S. Cl. .................. 356/607; 356/601; 356/606
(58) Field of Classification Search ......... 356/601–908; 73/146
See application file for complete search history.

(56) References Cited

U.S. PATENT DOCUMENTS

| | | | | |
|---|---|---|---|---|
| 3,918,816 | A * | 11/1975 | Foster et al. ................ | 356/602 |
| 4,910,411 | A * | 3/1990 | Teraguchi et al. ...... | 250/559.44 |
| 5,054,918 | A | 10/1991 | Downing et al. | |
| 5,060,173 | A * | 10/1991 | Tsuji ........................... | 73/146 |
| 5,103,595 | A | 4/1992 | Dale et al. | |
| 5,206,720 | A * | 4/1993 | Clothiaux et al. ............. | 348/95 |
| 5,245,867 | A | 9/1993 | Sube et al. | |
| 5,485,406 | A * | 1/1996 | Wada et al. ................... | 73/146 |
| 5,506,683 | A | 4/1996 | Yang et al. | |
| 5,636,026 | A * | 6/1997 | Mian et al. .................. | 356/602 |
| 5,987,978 | A | 11/1999 | Whitehead | |
| 6,069,966 | A | 5/2000 | Jones et al. | |
| 6,535,281 | B2 | 3/2003 | Conheady et al. | |
| 6,539,295 | B1 * | 3/2003 | Katzen et al. ................ | 701/29 |
| 6,680,471 | B2 * | 1/2004 | Kokubu et al. .............. | 250/225 |

(Continued)

FOREIGN PATENT DOCUMENTS

EP  0 547 365 A2  6/1993

(Continued)

*Primary Examiner*—Gregory J Toatley, Jr.
*Assistant Examiner*—Juan D Valentin
(74) *Attorney, Agent, or Firm*—McDermott Will & Emery LLP

(57) ABSTRACT

A method and apparatus for optically scanning a pneumatic tire of a vehicle wheel that is rotatably mounted on a measuring shaft of a wheel balancing machine. A light source, such as a laser beam source, is provided to emit at least one light beam onto the surface of the pneumatic tire, which is reflected by the surface and received by a receiver. In response, the receiver produces position signals based on the impingement point of the reflected beam for evaluation by a computer-aided evaluation device. Rotary angle signals representing the rotational angle of the wheel are supplied to the computer-aided evaluation device by a rotary angle sensor. The computer-aided evaluation device determines dimensions and positions of the pneumatic tire or its constituent parts based on the positional signals and the rotary angle signals.

6 Claims, 1 Drawing Sheet

U.S. PATENT DOCUMENTS

2002/0018218 A1 * 2/2002 Conheady et al. ........... 356/602

FOREIGN PATENT DOCUMENTS

| | | |
|---|---|---|
| EP | 0 565 320 A2 | 10/1993 |
| EP | 0 816 799 A2 | 1/1998 |
| EP | 0 884 574 A2 | 12/1998 |
| EP | 1 174 698 A2 | 1/2002 |
| WO | WO 96/10727 | 4/1996 |
| WO | WO 00/42409 | 7/2000 |

* cited by examiner

METHOD AND APPARATUS FOR OPTICALLY SCANNING A PNEUMATIC TIRE OF A VEHICLE WHEEL

RELATED APPLICATIONS

This application is related to a co-pending patent application Ser. No. 10/765,206, titled "METHOD OF MATCHING A VEHICLE WHEEL," filed concurrently herewith; a co-pending patent application Ser. No. 10/765,275, entitled "METHOD AND APPARATUS FOR BALANCING A MOTOR VEHICLE WHEEL," filed concurrently herewith; and a co-pending patent application Ser. No. 10/765,274, entitled "METHOD AND APPARATUS FOR OPTICALLY SCANNING A VEHICLE WHEEL," filed concurrently herewith. All of the applications are commonly assigned to the assignee of this application, and are incorporated herein by reference in their entireties.

FIELD OF THE DISCLOSURE

The disclosure concerns a method and apparatus for optically scanning a pneumatic tire of a vehicle wheel, and in particular, a method and apparatus for scanning a motor vehicle wheel, which is mounted rotatably about a stationary axis, by means of one or more light beams.

BACKGROUND AND SUMMARY OF THE DISCLOSURE

It is known that a tire tread surface can be scanned with a flat light beam to form an image of a strip-shaped profile of the tread surface and record it with a camera. An example of sensors that can be used to scan a tire tread surface is described in U.S. Pat. No. 6,535,281, titled "METHOD AND APPARATUS FOR OPTICALLY SCANNING A VEHICLE WHEEL," the entire disclosure of which is incorporated herein by reference. The sensor device includes a light source for emitting a light beam, and a light sensitive receiver for sensing lights. The light source and the receiver move synchronously. The surface of a motor vehicle wheel is scanned by a light beam emitted from the light source. The reflected beam is received by the light-sensitive receiver. The spacing of the scanned location of the wheel with respect to a reference location is determined based on the directions of the emitted beam and the reflected beam.

This disclosure describes methods and apparatus for comprehensively ascertaining the nature of the pneumatic tire of a motor vehicle wheel with improved efficiency. A vehicle wheel under test is mounted rotatably to a measuring shaft of a wheel balancing machine. At least one light beam, such as a laser beam, is directed from a light source disposed at a given position on to the surface of the pneumatic tire. The at least one light beam is reflected from the surface of the pneumatic tire and received by a light-sensitive receiver disposed at a given position. A sensor device includes the light source and the light-sensitive receiver may be used to scan the tread surface of the pneumatic tire. Dimensions and positions of the pneumatic tire or constituent parts of the pneumatic tire are ascertained based on the directions of the at least one emitted light beam and the reflected light beam.

To scan the two side walls of a tire and the tread thereof, it is possible to use a single sensor device that has the light source and the receiver on a common carrier. Alternatively, three sensor devices, each having the light source and the receiver on a common carrier, may be provided to each different surfaces of the tire. For example, a sensor device may be associated with the inside tire side wall, the outside tire side wall, and the tread surface, respectively.

A plurality of surface locations and/or spots on the pneumatic tire is scanned in succession when the tire is rotated. Dimensions and positions of the pneumatic tire or constituent parts of the pneumatic tire are ascertained based on the directions of the emitted light beam and the reflected light beam. Based on the dimensions and positions of the pneumatic tire or constituent parts of the pneumatic tire, it is possible to detect irregular wear of the tire or the tire profile depth at the tread surface as well as unacceptable conicity of the tread surface. Based on the profile depth, it is possible to ascertain the probable period of use of the tire, up to a required tire change. In addition, it is possible to ascertain irregular tire wear such as abrasion tracks extending crosswise or flat abrasion tracks on parts of the tread surface as well as tire shoulder wear and irregular tire shoulders and the like. In addition, scanning the side walls of the tire makes it possible to detect indentations or bulges in those parts of the tire. It is also possible to detect an irregular fit of the tire in the rim base.

Additional aspects and advantages of the present disclosure will become readily apparent to those skilled in this art from the following detailed description, wherein only exemplary embodiments of the present disclosure is shown and described, simply by way of illustration of the best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The accompanying drawings, which are incorporated in and constitute a part of the specification, illustrate exemplary embodiments.

DETAILED DESCRIPTION OF THE DISCLOSURE

Figure 1:
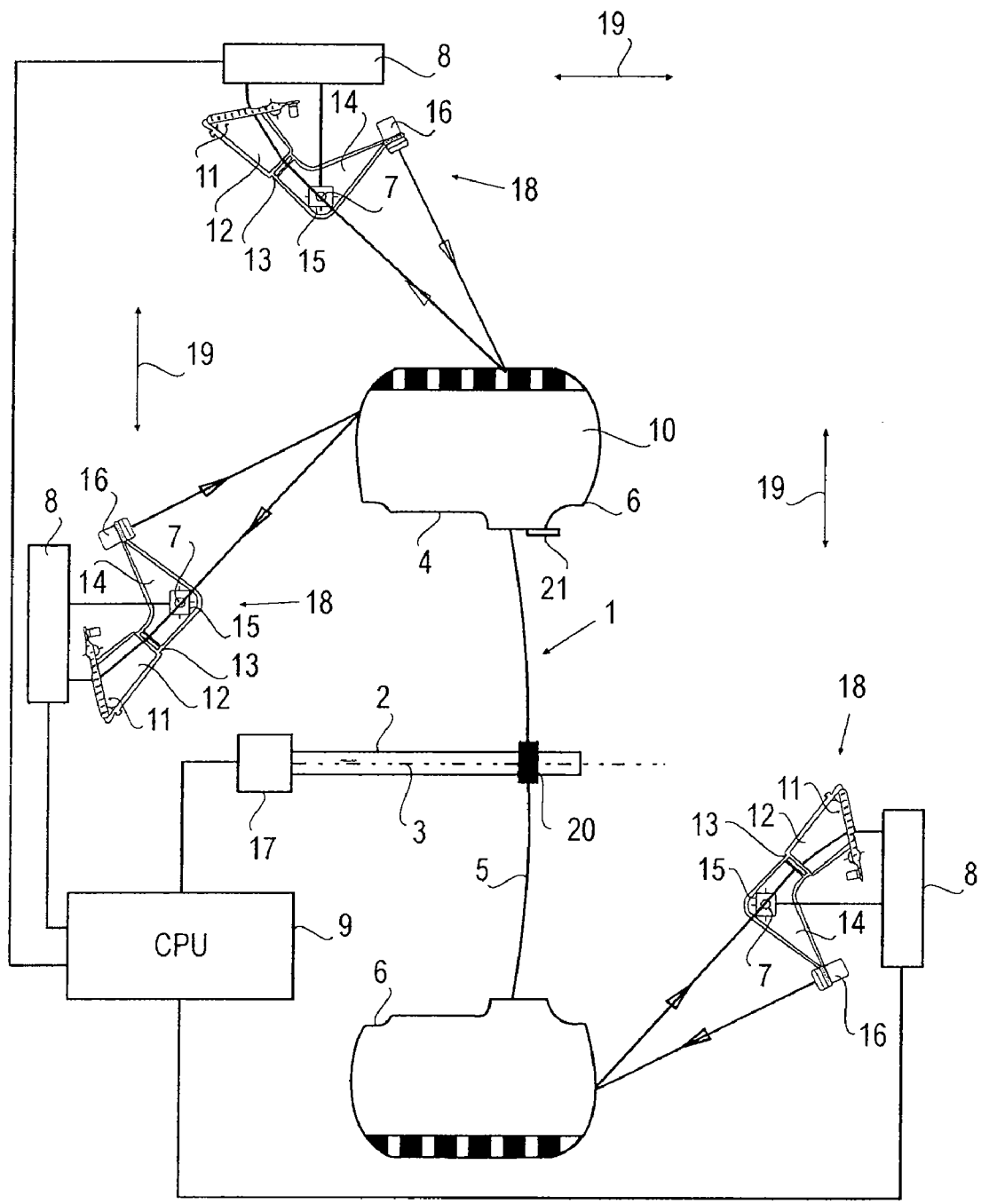
FIG. 1 depicts an exemplary system for comprehensively ascertaining the nature of the pneumatic tire of a motor vehicle wheel.

In the following description, for the purposes of explanation, numerous specific details are set forth in order to provide a thorough understanding of the present disclosure. It will be apparent, however, to one skilled in the art that the present disclosure may be practiced without these specific details. In other instances, well-known structures and devices are shown in block diagram form in order to avoid unnecessarily obscuring the present disclosure.

FIG. 1 shows an exemplary system for comprehensively ascertaining the nature of the pneumatic tire of a motor vehicle wheel. In FIG. 1, a vehicle wheel 1 is shown with a wheel disc portion 5 and a rim 4 fixed to the periphery of a wheel disc portion 5. A pneumatic tire 10 is mounted on a rim 4. Tire beads are supported in known manner at rim flanges 6 of the rim 4. The vehicle wheels can be any kind, such as motor vehicle wheels, motorcycle wheels, trucks, buses, and the like.

The vehicle wheel 1 is fixed in a known manner to a measuring shaft 2 of a wheel balancing machine (not shown) at a fixed location 20, and is supported rotatably about an axis of rotation that is defined by the measuring shaft 2. The axis, when the wheel is clamped in position in centered relationship, coincides with a wheel axis 3, which ensures that the wheel axis 3 is stationary on the wheel balancing machine.

The dimensions and positions of constituent parts of the pneumatic tire 10 can be measured with one or more sensor devices 18 and ascertained by a data processing system, such as a computer. Each sensor device 18 includes a light source 16, such as a laser. In addition, each sensor device 18 includes a receiver 12, such as a CCD-sensor, as a position-sensitive receiving element. The light source 16 and the receiver 12 are attached to a carrier 14. The carrier 14 is supported pivotably about a pivot axis 17. The carrier 14 can also be movably mounted linearly (double-headed arrow 19) or on a predetermined guide path with respect to the measuring shaft 2 and the fixing 20 of the vehicle wheel 1 to the measuring shaft 2. The pivotal movement and the optionally additional linear or guided movement can be implemented by means of a drive (not shown), for example in the form of one or more stepping motors. A receiver optical system 13 is also provided on the carrier 14. The receiver optical system 13 and the CCD-sensor 11 are constituent parts of the receiver 12.

The light source 16 emits a light beam on to the surface of the pneumatic tire 10 and forms a light spot on the surface. The light beam is reflected and passes through the focusing receiver optical system 13 on to the sensor elements of the CCD-sensor 1. The CCD-sensor 11 can detect a plurality of local maxima of an illumination intensity function, each of the local maxima is independent from each other. The direction of the reflected beam depends on the distance of the location scanned on the pneumatic tire 10, relative to the light source 16 and to the receiver 12. Based on that distance, the reflected beam is directed by the receiver optical system 13 on to a given location of the CCD-sensor 11, and is then converted into a position-sensitive or position-dependent signal. That signal is passed to an electronic measuring apparatus 8 that is coupled to a position sensor 15. The position sensor 15 supplies the electronic measuring apparatus 8 with position signals that are representing to the respective positions of the light source 16 and the CCD-sensor 11. In one embodiment, the light source 16 and the receiver 12 are movable together with each other as they are fixed to the common carrier 14. The position signals are in reference to a reference position on the wheel balancing machine (not shown). Since the measuring shaft 2 is affixed in stationary to the wheel balancing machine, the position signals are thus related to the measuring shaft 2 and to the axial fixing location 20 at which the vehicle wheel 1 is attached to the measuring shaft 2. The electronic measuring apparatus 8 produces measurement signals corresponding to the positions of the surface locations (spots) of the pneumatic tire 10, which are scanned by the light beams emitted by the light source 16.

The surface locations of the pneumatic tire 10 can be detected by three sensor devices 18, each of which is associated with the inside (left-hand sensor device 18 in FIG. 1), the outside (right-hand sensor device 18 in FIG. 1), and the tread surface (upwardly disposed sensor device 18 in FIG. 1) of the pneumatic tire 10, respectively. Examples of sensor devices 18 are described in U.S. Pat. No. 6,535,281, which is incorporated in this application by reference previously. It is however also possible to use only one sensor device 18 that moves into suitable measuring positions on a predetermined guide path to the inside, the outside, and the tread surface of the pneumatic tire 10.

In order to detect all surface spots of the vehicle wheel 1, the wheel 1 is mounted rotatably to the measuring shaft 2, which coincides with the wheel axle 3. The electronic measuring apparatus 8 that furnishes the corresponding measurement signals can be a constituent part of the respective sensor device 18. It is however also possible for the electronic measuring apparatus 8 to be integrated into an evaluation device 9, such as a computer, which operates in computer-aided fashion. Dimensions and positions of constituent parts of the pneumatic tire 10 as well as properties of those constituent parts can be determined and evaluated by the evaluation device 9 in a computer-aided procedure.

The respective rotary angle position of the pneumatic tire 10 can be determined by a rotary angle sensor 17 connected to the measuring shaft 2 of the wheel balancing machine. The sensor 17 supplies rotary angle increments to the evaluation device 9 representing the rotary movement of the motor vehicle wheel 1. The rotary angle increments provide positional information of the respective rotary angle positions of the surface location of the tire surface, which is being scanned by the respective sensor device 18. A tire inflation valve 21 can serve as the reference for determining rotary angles by the sensor device 18 that scans the outside of the vehicle wheel.

The sensor device 18 associated with the inside of the vehicle wheel may be mounted to the housing of the wheel balancing machine, such as beneath the measuring shaft 2. The sensor device 18 for scanning of the tread surface of the pneumatic tire 10 can be disposed in the proximity of a pivot axis of a wheel guard hood that, in the measuring run, is pivoted into a position over the rotating wheel. The sensor device 18 associated with the outside of the vehicle wheel 1 can be arranged on the pivotable wheel guard hood or connected thereto.

As can be seen from FIG. 1, the side walls, i.e., the inward and the outward side surfaces of the pneumatic tire 10, as well as the tread surface of the pneumatic tire 10, can be scanned with the three sensor devices 18. The region of the tire shoulders can also be detected. As already explained earlier, with the scan information, it is possible to detect rotary angle-related abrasion points and flat spots, unevenness, and defects on the tire caused by abrasion, wear and the like.

The disclosure has been described with reference to specific embodiments thereof. It will, however, be evident that various modifications and changes may be made thereto without departing from the broader spirit and scope of the disclosure. The concepts described in the disclosure can apply to various operations of the networked presentation system without departing from the concepts. The specification and drawings are, accordingly, to be regarded in an illustrative rather than a restrictive sense.

What is claimed is:

1. A method of optically scanning a pneumatic tire of a vehicle wheel the method comprising the steps of:
   rotating the vehicle wheel about a stationary axis;
   scanning the surface of the pneumatic tire while the wheel is rotating by emitting three light beams from three given positions onto the surface of the pneumatic tire forming a light spot in each given position;
   receiving three beams reflected by the surface of the pneumatic tire corresponding to each of the three light beams for measuring the distance of each of the light spots relative to a reference position;
   measuring a rotary angle position of the vehicle wheel associating with the measured distances; and
   determining dimensions and positions of the pneumatic tire or constituent parts of the pneumatic tire based on the measured distances of the three light spots and the associated rotary angle position of the vehicle;
   wherein one of the light beams scans the tire tread surface, and the other two of the light beams scans the tire side walls at the inside and the outside of the wheel such that all external surface spots of the tire are scanned.

2. The method according to claim 1, wherein the profile depth and/or irregular tire wear are ascertained when scanning the tread surface.

3. The method according to one of claim 2, wherein the tread surface of the pneumatic tire is scanned to determine unacceptable conicity.

4. The method according to claim 1 further comprising the step of detecting the tire fit on the tire rim and/or indentations and/or bulges at one or both tire side walls of the wheel, based on the respective directions of at least one of the emitted light beams and at least one of the reflected beams.

5. An apparatus for optically scanning a pneumatic tire of a vehicle wheel that is rotatably mounted on a measuring shaft of a wheel balancing machine, comprising:

three sensor devices, each comprising a light source that emits a light beam configured to scan the surface of the pneumatic tire while the wheel is rotating to form at least one light spot on the tire surface, and a receiver movable together with the light source, wherein the receiver is configured to receive a beam reflected by the surface of the pneumatic tire while the wheel is rotating, and produce a signal based on the receiving position of the reflected beam at the receiver, and wherein each light source and corresponding receiver are movable together into given positions relative to the measuring shaft for measuring the distance of the at least one light spot relative to a reference position;

a rotary angle sensor, coupled to the measuring shaft, for generating a rotary angle associated with the at least one light spot of each sensor based on the rotation of the measuring shaft and the vehicle wheel; and a computer-aided evaluation device, coupled to the rotary angle sensor and the receivers, for ascertaining dimensions and positions of the pneumatic tire or constituent parts of the pneumatic tire based on the measured distance of the at least one light spot of each sensor and the associated rotary angle position of the rotating vehicle wheel;

wherein one of the sensor devices is configured to scan the tire tread surface, and the other two of the sensor devices are configured to scan the tire side walls at the inside and the outside of the wheel such that all external surface spots of the tire are scanned, and the sensor devices are attached to movable components of a wheel balancing machine.

6. A method using three light beams for optically scanning a pneumatic tire of a vehicle wheel that is rotatably mounted to a stationary axis, in which a light beam is directed from each of three given positions on to the surface of the pneumatic tire while the wheel is rotating, and an associated reflected beam is received at each of the three given positions, wherein dimensions and positions of the pneumatic tire or constituent parts of the pneumatic tire are ascertained based on the directions of the emitted light beams and the reflected beams;

wherein one of the light beams scans the tire tread surface, and the other two of the light beams scans the tire side walls at the inside and the outside of the wheel such that all external surface spots of the tire are scanned.

* * * * *